United States Patent
Takahashi et al.

(10) Patent No.: US 7,374,357 B2
(45) Date of Patent: May 20, 2008

(54) PLUGGING TYPE DENTAL LIQUID HOUSING CONTAINER

(75) Inventors: Masayuki Takahashi, Itabashi-ku (JP);
Shigeru Igarashi, Itabashi-ku (JP);
Shinichi Kojima, Itabashi-ku (JP)

(73) Assignee: GC Corporation, Tokyo (JP)

( * ) Notice: Subject to any disclaimer, the term of this patent is extended or adjusted under 35 U.S.C. 154(b) by 338 days.

(21) Appl. No.: 11/316,745

(22) Filed: Dec. 27, 2005

(65) Prior Publication Data
US 2006/0154523 A1   Jul. 13, 2006

(30) Foreign Application Priority Data
Jan. 12, 2005   (JP) ............................. 2005-005357

(51) Int. Cl.
*A46B 11/00* (2006.01)
*B65D 41/00* (2006.01)
*B65D 39/00* (2006.01)

(52) U.S. Cl. ................. 401/118; 401/126; 215/45; 215/296; 215/305; 215/355

(58) Field of Classification Search ................ 401/118, 401/126, 128, 130; 277/630, 609, 603, 615; D9/439, 443; 215/43, 45, 46, 215, 296, 305, 215/355, 356, 363, 321, 329, 330
See application file for complete search history.

(56) References Cited

U.S. PATENT DOCUMENTS

| | | | | |
|---|---|---|---|---|
| 3,910,444 A | * | 10/1975 | Foster | 215/295 |
| 4,108,325 A | * | 8/1978 | Barre | 215/364 |
| 5,944,208 A | * | 8/1999 | Gale | 215/296 |
| 6,957,958 B2 | * | 10/2005 | Rowe et al. | 433/89 |

* cited by examiner

*Primary Examiner*—David J. Walczak
(74) *Attorney, Agent, or Firm*—Oblon, Spivak, McClelland, Maier & Neustadt, P.C.

(57) ABSTRACT

For sure sealing and easy handling, the plugging type dental liquid housing container comprises a container main body 1 having a holding blade plate projected on an outer circumference of a liquid housing part 1a; a flat face 1ea, a slope face 1eb and a stepped face 1ec at of an opening end; and an inner face taper part 1d provided on the opening side of an inner face 1c of the liquid housing part 1a so as to have an inner diameter gradually decreasing toward the bottom side, and a plug body 2 having a contacting blade plate 2b projected on an outer circumference thereof; a truncated conical shape part 2e at a bottom; and plural annular projection ridge parts 2f formed above truncated conical shape part 2e so as to contact with a portion on the bottom side of the inner face taper part 1d.

14 Claims, 5 Drawing Sheets

PLUGGING TYPE DENTAL LIQUID HOUSING CONTAINER

BACKGROUND OF THE INVENTION

1. Field of the Invention

The present invention relates to a plugging type dental liquid housing container capable of firmly sealing by plugging, hardly causing liquid leakage or the like, and easily opening by only rotating a plugged plug body without soiling a hand.

2. Description of the Conventional Art

In the dental liquid housing container, sufficient care is necessary in order not to leak a chemical or the like inside thereof and expose it with external air, and sealability is remarkably important as compared with the general container. Therefore, the plug body inserted and fitted into an opening part of the container is used in many cases without using a cap type cover body. However, although the high sealability can be kept by the plug body, there is a problem that it takes time and effort for opening the container.

Further, since the chemical used for a dental treatment is comparatively little, the dental liquid housing container is a small type in general, and thus there is a problem that the handling of opening or the like is difficult. Therefore, when the plug body is used in order to increase the sealability, the handling becomes more difficult. Thus, in the conventional dental liquid housing container, it is remarkably difficult to keep the high sealability together with the easy handling using the plug body.

For solving such the problem, the following opening and closing cap of the container has been used (for example, Japanese Utility Model Laid Open No. 60-142742). It is an opening and closing cap comprising a fitting cylindrical body and a plug body. The fitting cylindrical body is fixed at a pour-out neck part protruded from a barrel part of the container, and the plug body is detachable with the fitting cylindrical body. In this opening and closing cap, the fitting cylindrical body comprises a sleeve inserted in the pour-out neck part, and plural of first protruded pieces separately formed on the upper face of an outer circumference of the sleeve. The plug body comprises a top plate having a diameter equal to an outer diameter of the cylindrical body or more, a sleeve provided downward from the lower face of the top plate, a plug core liquid-tightly fitted with the sleeve, and plural second protruded pieces separately formed on the lower face of the top plate at the outer circumference of the plug core. When the top plate of the plug body is rotated, the second protruded piece is run upon the first protruded piece to generate lifting force, and the fitting of an annular projection with a stepped part or a recessed groove is released by the rising force. However, as for this opening and closing cap, the structure is complicated, and the fitting cylindrical body and the plug body must be inserted into the opening part of the container. Thus, although this cap can be used to a comparatively large makeup bottle or the like, it cannot be used to the small type dental liquid housing container. Further, when the structure as in this opening and closing cap, where the plural first protruded pieces and second protruded pieces are separately formed on the lower face of the plug body and the upper face of the fitting cylindrical body respectively and the second protruded piece of the plug body is run upon the first protruded piece of the fitting cylindrical body, to thereby open the cap, is used to the small type dental liquid housing container, the first protruded piece and the second protruded piece cannot be formed largely and the plug body can hardly be lifted to the sufficient height. Thus, contacting length of the fitting cylindrical body and the plug body cannot be sufficiently secured to have high sealability.

Further, as for a cap not using such the two kinds of protruded pieces, the following cap structure has been used (Japanese Utility Model Laid Open No. 3-100141). It is a cap structure comprising a cylindrical neck part having upper and lower openings and a cap detachably mounted to the neck part. The cylindrical neck part is provided at an upper end part of the container. In this structure, an inner circumference part of the neck part has an approximately elliptical shape at an upper portion and is gradually contracted toward the lower portion to have an approximately right circle. As for the cap, the plug body capable of inserting into the neck part is integrally formed downward from a lower face center part, and a base end of the plug body has the approximately same elliptical shape as the upper portion of the neck part. In the cap structure of the container, the upper portion of the inner circumference part of the neck part and the base end of the plug body formed downward form the cap are formed to have the elliptical shape. By rotating the cap where the plug body is formed downward, the portions having the elliptical shapes are not engaged each other, to thereby push up the plug body inserted into the neck part. However, as for this cap structure of the container, the neck part and the plug body of the cap must be inserted into the opening part of the container and the sufficiently large opening part is needed to make the inner circumference part or the like of the neck part to have an elliptical shape, corresponding to the major axis of the ellipse. Thus, this structure can not be used at all to the small type dental liquid housing container.

SUMMARY OF THE INVENTION

The present invention solves the above-mentioned problems, and the primary objective of the present invention is to provide the plugging type dental liquid housing container capable of firmly sealing by plugging, hardly causing the liquid leakage or the like, and easily opening by only rotating the plugged plug body without soiling a hand.

The earnest work was carried out in order to solve the above-mentioned problems and, as a result of this, the followings were found to complete the present invention. It is a plugging type dental liquid housing container comprising a container main body having a holding blade plate for holding the container, which is projected on an outer circumference face of a cylindrical liquid housing part having an opening upper end and a closing bottom part, and a plug body having a sealing plug part at a lower end thereof and a contacting blade plate for contacting with an end face of an opening part, which is projected on an outer circumference face of the plug main body starting from the upper end of the sealing plug part. In such the plug type dental liquid container, since only the sealing plug part of the plug body is inserted and fitted to the opening part of the container main body, even a comparatively small plugging type dental liquid housing container can be sufficiently sealed. Further, the followings are found out by taking notice of the end face of the opening part capable of securing the longest distance in the opening part of the container main body. When a slope face is formed at the end face of the opening part, by rotating the plug body, the end face on the plug main body side, which is the lower face of the contacting blade plate provided on the plug body, is guided by this slope face, and thereby the plug body is lifted to the sufficient height. Thus, the plug body can be inserted and fitted to the sufficient depth in the container main body to thereby secure high sealability, and the structure is made simple so that the container can be produced easily. Further, by holding only the holding blade plate on the outer circumference face of the container main body and the contacting blade plate on the outer circumference face of the plug body by both hands, and rotating them, the container can be opened easily, and thus the handling is remarkably improved. Further, since the plug body can be rotated with a sufficient force, the plug body can be opened easily even when it is firmly inserted and fitted into the container main body. Further, when plural annular projection ridge parts are formed at the sealing plug part of the plug body, each annular projection ridge part being flexible bent in a space between the annular projection ridge parts when plugging, each annular projection ridge part can be deformed and closely fitted to the inner face of the liquid housing part of the container main body, and further, the opening part of the container body is multiply sealed with such the plural annular projection ridge parts, so that the sufficient sealability can be secured.

That is, the plugging type dental liquid housing container according to the present invention comprises a container main body having a holding blade plate projected on an outer circumference of a cylindrical liquid housing part which has an opening upper end and a closing bottom part, and a plug body having a the sealing plug part at a lower end thereof and a contacting blade plate projected on an outer circumference face of a plug main body which is provided starting from an upper end of the sealing plug part.

The container main body has a flat face, a slope face and a stepped face at an end face of an opening end of the liquid housing part respectively, and an inner face taper part on an opening part side of an inner face of the liquid housing part. The flat face is rectangular with a center axis of the liquid housing part, and is contacted with the end face on the plug main body side of the lower face of the contacting blade plate, when the plug body is plugged. The slope face is inclined to be raised in the predetermined direction from one end of the flat face. The stepped face is fallen to another end of the flat face from a top point of the slope face. The inner face taper part has an inner diameter gradually decreasing toward the bottom part side from at least the flat face.

The sealing plug part of the plug body has a truncated conical shape part tapered toward the lower end, and plural annular projection ridge parts on the upper side of the truncated conical shape part. The plural annular projection ridge parts are contacted with a portion on the bottom part side of the inner face taper part of the inner face of the liquid housing part of the container main body, and positioned at the inner face taper part of the liquid housing part when the plug body is rotated to move the end face of the contacting blade plate along the slope face of the end face of the opening end of the liquid housing part to the top point of the slope face.

Further, the plug body taper part, which is contacted with the inner face taper part of the liquid housing part, is formed on the upper side of the annular projection ridge parts of the sealing plug part of the plug body. In such a constitution, when the plug body is plugged, the inner face taper part of the liquid housing part is contacted and closely fit with a plug body taper part of the sealing plug part of the sealing body, and thus the opening part of the container main body is sealed by not only the annular projection ridge parts formed at the sealing plug part of the plug body but also the plug body taper part. Then, the sealability is enhanced, so that it is preferable. Further, the end faces of contacting blade plates may be projected respectively at one pair of positions facing each other on the plug main body of the plug body, and the flat faces, the slope faces and the stepped faces are respectively formed at one pair of positions facing each other on the end face of the opening ends of the liquid housing part. In such a constitution, each of the contacting blade plates, which are projected at one pair of positions facing each other, is moved along each slope face formed on the opening end of the liquid housing part. Thus, since the plug main body of the plug body is pushed upwardly at one pair of positions facing each other, the plug body is lifted uprightly without falling sideways. Therefore, the container can be opened smoothly and easily only by half rotating the plug body, so that it is preferable. Further, a holding blade plate for holding the plug body may be further projected on the outer circumference face at the upper side from the sealing plug part of the plug main body so as not to contact with the container main body when the plug body is plugged or removed. In such a constitution, when the contacting blade plate has a shape which is hardly held or the number of the blade is a few, the plug body can be firmly held to be certainly rotated by the separately provided holding blade plate for holding the plug body, so that it is preferable.

Further, in order to keep the high sealability, it is preferable that the container body or the plug body is formed with a material having low temperature dependency and capable of keeping rigidity even at high temperature. In addition, there may be a problem that the container can not be opened by self-fusing of the container main body and the plug body. Therefore, when the liquid housed in the liquid housing part is a dental liquid dissolved with an organic solvent having high volatility, it is preferable that the container main body is made of a mixture of an ethylene-tetracyclododesene copolymer of 90% or more by weight and polyethylene, the plug body is made of a mixture of an ethylene-tetracyclododesene copolymer of 50% or more by weight and polyethylene, and at least one of ethylene-tetracyclododesene copolymer contained in the container main body and the plug body is less than 95% by weight. Since the container main body, which is generally susceptible to the temperature change when exposing it to the external air, is formed with the material comprising the ethylene-tetracyclododesene copolymer of 90% or more by weight, the temperature dependency is low and the high rigidity can be kept even at high temperature. Further, the plug body inserted into the container main body is not susceptible to the external temperature influence in general. Thus, when the plug body is formed with the material comprising the ethylene-tetracyclododesene copolymer of 50% or more by weight, the high rigidity can be sufficiently kept. Further, since at least one of ethylene-tetracyclododesene copolymer contents of the container main body and the plug body is less than 95% by weight, the container main body and the plug body are not self-fused each other, so that it is preferable.

Further, the container further may comprise a liquid taking out tool where a liquid adsorbent is mounted on one end of a rod-shaped part which extends to the bottom part of the liquid housing part when the rod-shaped part is inserted into the liquid housing part of the container main body. In such a constitution, liquid can be taken out easily even if there is a small amount of the liquid remaining in the container main body. Further, if the liquid absorbed by the liquid adsorbent is used as it is, the dental treatment can be carried out without soiling the hand, so that it is preferable.

The plugging type dental liquid housing container of the present invention comprises the container main body and the plug body. The container main body having the holding blade plate projected on the outer circumference of the cylindrical liquid housing part which has the opening upper end and the closing bottom part, and the plug body having the sealing plug part at the lower end thereof and the contacting blade plate projected on the outer circumference face of the plug main body which is provided from the upper end of the sealing plug part. Thus, since only the plug body is inserted and fitted into the opening part of the container main body, the plugging type dental liquid housing container, which is comparatively small, can be sealed sufficiently. Further, since the holding blade plate and the contacting blade plate are respectively projected on each outer circumference face of the liquid housing part of the container main body and the plug body, the container can be easily opened only by rotating these blade-shaped parts by holding them with both hands. Thus, not only the handling is remarkably improved, but also the plug body can be rotated by sufficient force, so that the container can be easily opened even when the plug body is firmly inserted and fitted into the container main body.

Further, the container main body has the flat face, the slope face and the stepped face at the end face of the opening end of the liquid housing part respectively, and the inner face taper part on the opening part side of the inner face of the liquid housing part, in which the flat face is rectangular with the center axis of the liquid housing part, and is contacted with the end face on the plug main body side of the lower face of the contacting blade plate, when the plug body is plugged, the slope face is inclined to be raised in the predetermined direction from one end of the flat face, the stepped face is fallen to another end of the flat face from a top point of the slope face, and the inner face taper part has an inner diameter gradually decreasing toward the bottom part side from at least the flat face. Thus, by forming the slope face for lifting the plug body on the end face of the opening part, where the longest distance can be secured, of the container main body, the plug body can be lifted to the sufficient height even when having a small type opening part. Thus, the plug body can be inserted and fitted to the sufficient depth in the container main body, sufficient contacting length of the fitted cylindrical body and plug body can be secured and sealability can be thereby enhanced, as well as the structure is made simple to be produced easily.

Further, the sealing plug part of the plug body has the truncated conical shape part tapered toward the lower end, and the plural annular projection ridge parts on the upper side of the truncated conical shape part, in which the plural annular projection ridge parts are contacted with a portion on the bottom part side of the inner face taper part of the inner face of the liquid housing part and positioned at the inner face taper part of the liquid housing part when the plug body is rotated to move the end face of the contacting blade plate along the slope face of the end face of the opening end of the liquid housing part to the top point of this slope face. Thus, since each annular projection ridge part is flexible in the space between the annular projection ridge parts when plugging, each annular projection ridge part can be deformed and closely fitted to the inner face of the liquid housing part, and thereby, the opening part of the container body is multiply sealed with such the plural annular projection ridge parts, so that the sufficient sealability can be secured. Further, since the opening part of the container main body is sealed by the plural annular projection ridge parts until the holding blade plate moved along the slope face reaches the top point thereof by rotating the plug body after the plug body is plugged, sealability can be kept sufficiently.

Further, in a case that the plug body taper part, which is contacted with the inner face taper part of the liquid housing part of the container main body, is formed on the upper side of the annular projection ridge parts of the sealing plug part of the plug body, the inner face taper part of the liquid housing part is contacted and closely fitted with the plug body taper part of the sealing plug part when the plug body is plugged, the opening part of the container main body is sealed by not only the annular projection ridge parts formed on the sealing plug part of the plug body but also the plug body taper part. Thus, the sealability is enhanced. Further, in a case that the contacting blade plates are projected respectively at one pair of positions facing each other on the plug main body of the plug body, and the flat faces, the slope faces and the stepped faces are respectively formed at one pair of positions facing each other on the end face of the opening ends of the liquid housing part, each of the end faces of the contacting blade plates, which are projected at one pair of positions facing each other, is moved along each slope face formed at the opening end of the liquid housing part of the container main body. Thus, since the plug main body of the plug body is pushed upwardly at one pair of positions facing each other, the plug body is lifted uprightly without falling sideways. Therefore, the container can be opened smoothly and easily only by half-rotating the plug body. Further, in a case that the holding blade plate for holding the plug body is further projected on the outer circumference face on the upper side from the sealing plug part of the plug main body so as not to contact with the container main body when the plug body is plugged or removed, when the contacting blade plate has a shape which is hardly held or the number of the blade is a few, the plug body can be firmly held to be certainly rotated by the separately provided holding blade plates for holding the plug body.

Further, in a case that the liquid housed in the liquid housing part is a dental liquid dissolved with an organic solvent having high volatility, the container main body is made of a mixture of an ethylene-tetracyclododesene copolymer of 90% or more by weight and polyethylene, the plug body is made of a mixture of an ethylene-tetracyclododesene copolymer of 50% or more by weight and polyethylene, and at least one of ethylene-tetracyclododesene copolymer contained in the container main body and the plug body is less than 95% by weight, since the container main body, which is generally susceptible to the temperature change when exposing it to the external air, is formed with the material comprising the ethylene-tetracyclododesene copolymer of 90% or more by weight and thus the temperature dependency is low, the high rigidity can be kept even at high temperature. Further, the plug body inserted into the container main body is not susceptible to the external temperature influence in general. Thus, when the plug body is formed with the material comprising the ethylene-tetracyclododesene copolymer of 50% or more by weight, the high rigidity can be sufficiently kept. Further, when at least one of ethylene-tetracyclododesene copolymer contained in the container main body and the plug body is less than 95% by weight, the container main body and the plug body are not self-fused each other.

Furthermore, when the container further comprises the liquid taking out tool where the liquid adsorbent is mounted on one end of the rod-shaped part which extends to the bottom part of the liquid housing part when the rod-shaped part is inserted into the liquid housing part of the container main body, the liquid can be taken out easily even if there is a small amount of the liquid remaining in the container main body. Further, if the liquid absorbed by the liquid adsorbent is used as it is, the dental treatment can be carried out without soiling the hand.

DETAILED DESCRIPTION OF PREFERRED EMBODIMENT

Figure 1:
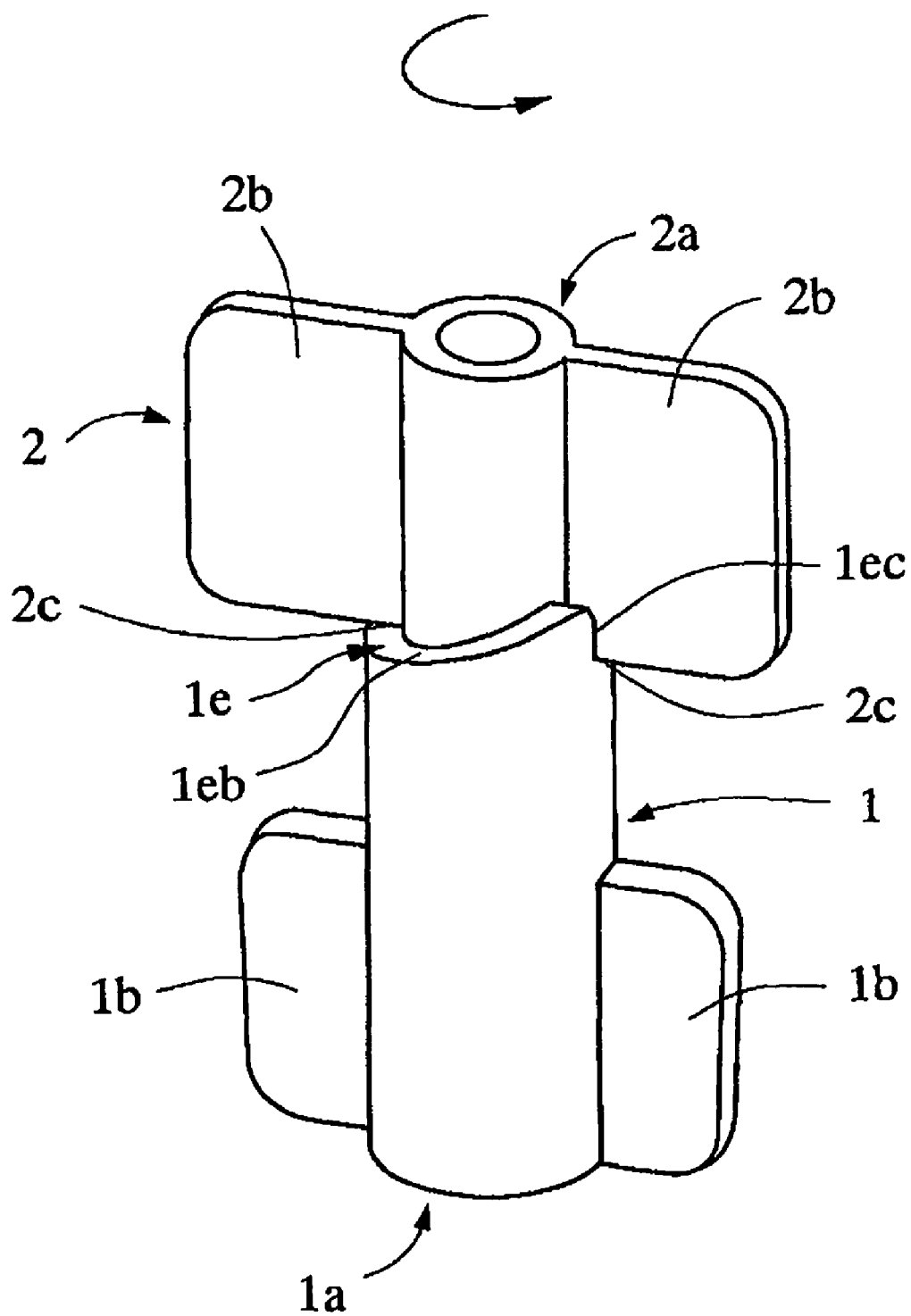
FIG. 1 is a perspective explanation view of one example of a plugging type dental liquid housing container according to the present invention.

Hereinafter, the plugging type dental liquid housing container according to the present invention is explained concretely with drawings.

In the drawings, 1 is a container main body, where a holding blade plate 1b is projected on the outer circumference face of a cylindrical liquid housing part 1a having an opening upper end and a closing bottom part. An end face 1e of the opening end of the liquid housing part 1a has a flat face 1ea, a slope face 1eb and a stepped face 1ec. The flat face 1ea is rectangular with a center axis of the liquid housing part 1a, and is contacted with an end face 2c at a plug main body 2a side of the lower face of the contacting blade plate 2b, when a plug body 2 mentioned below is plugged. The slope face 1eb is inclined to be raised in the predetermined direction from one end of the flat face 1ea. The stepped face 1ec is fallen to another end of the flat face 1ea from a top point of the slope face 1eb. An inner face taper part 1d is formed on the opening part side of an inner face 1c of the liquid housing part 1a, and has an inner diameter gradually decreasing toward the bottom part side from at least the flat face 1ea.

2 is a plug body having a sealing plug part 2d at a lower end thereof, and the contacting blade plate 2b projected on the outer circumference face of the plug main body 2a, which is provided from the upper end of the sealing plug part 2d. The sealing plug part 2d of the plug body 2 has a truncated conical shape part 2e tapered toward the lower end, and plural annular projection ridge parts 2f on the upper side of the truncated conical shape part 2e. The plural annular projection ridge parts 2f are contacted with the portion on the bottom part side of the inner face taper part 1d of the inner face 1c of the liquid housing part 1a of the container main body 1, and positioned at the inner face taper part 1d of the liquid housing part 1a, when the plug body 2 is rotated and the end face 2c of the contacting blade plate 2b is moved along the slope face 1eb of the end face 1e of the opening end to the top point of this slope face 1eb.

Further, a plug body taper part 2g, which is contacted with the inner taper part 1d of the liquid housing part 1a, is formed on the upper side of the annular projection ridge parts 2f of the sealing plug part 2d of the plug body 2. Thus, the inner face taper part 1d of the liquid housing part 1a is contacted and closely fitted with the plug body taper part 2g of the sealing plug part 2d of the plug body 2, and thereby the opening part of the container main body 1 is sealed by not only the plural annular projection ridge parts 2f formed on the sealing plug part 2d but also the plug body taper part 1d. By taking this constitution, the sealability is enhanced, and it is preferable. Further, a holding blade plate 2h, which is not contacted with the container main body 1 when the plug body 2 is plugged or removed, may be projected in addition on the outer circumference face on the upper side from the sealing plug part 2d of the plug main body 2a. In such a constitution, when the contacting blade plate 2b has a shape which is hard to hold or the number of the plates is a few, the plug body 2 can be firmly held to be certainly rotated by separately providing the holding blade plate for the plug body 2h, so that it is preferable.

Figure 2:
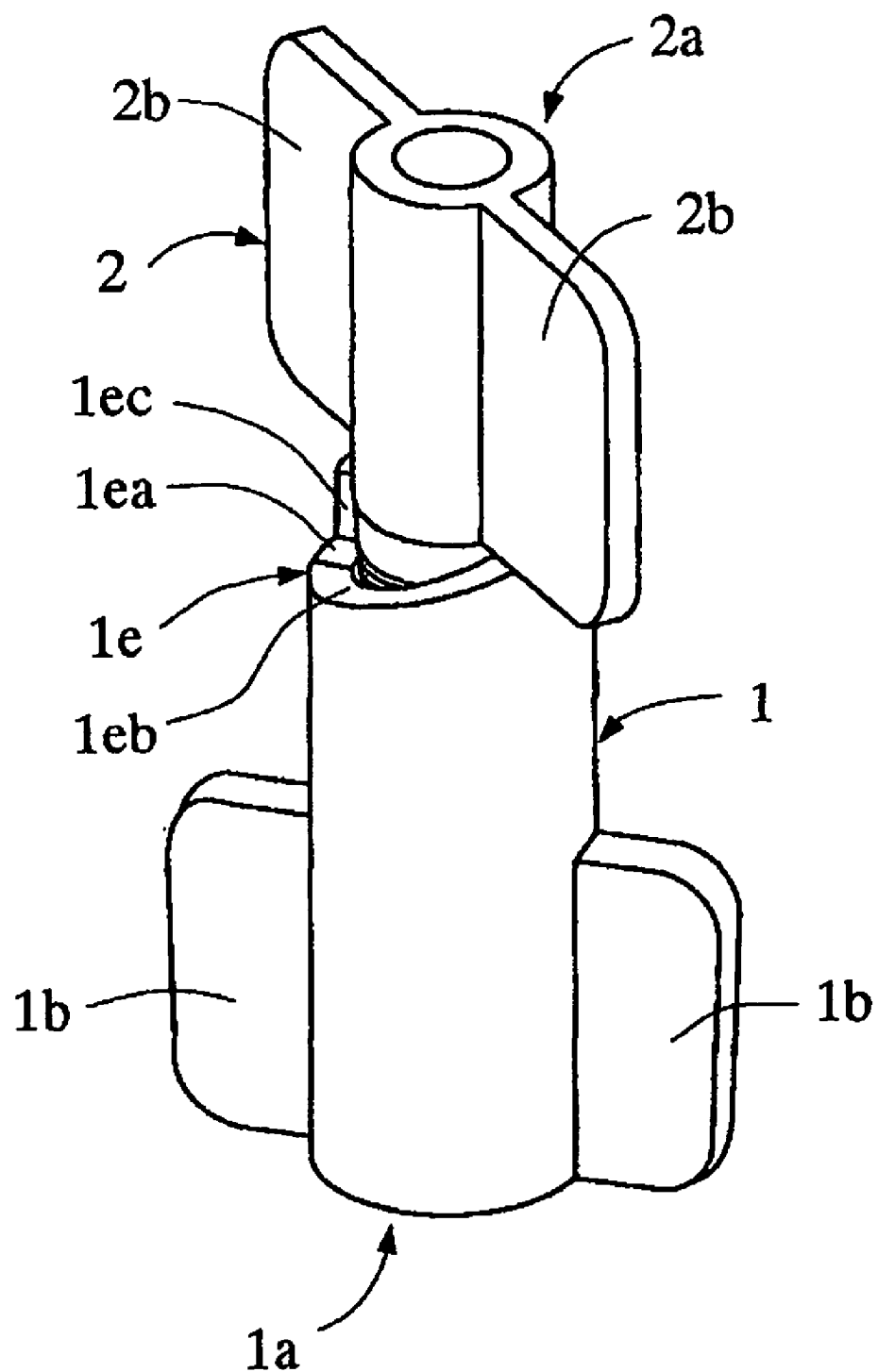
FIG. 2 is a perspective explanation view showing a state when opening the plugging type dental liquid housing container of FIG. 1.
Figure 3:
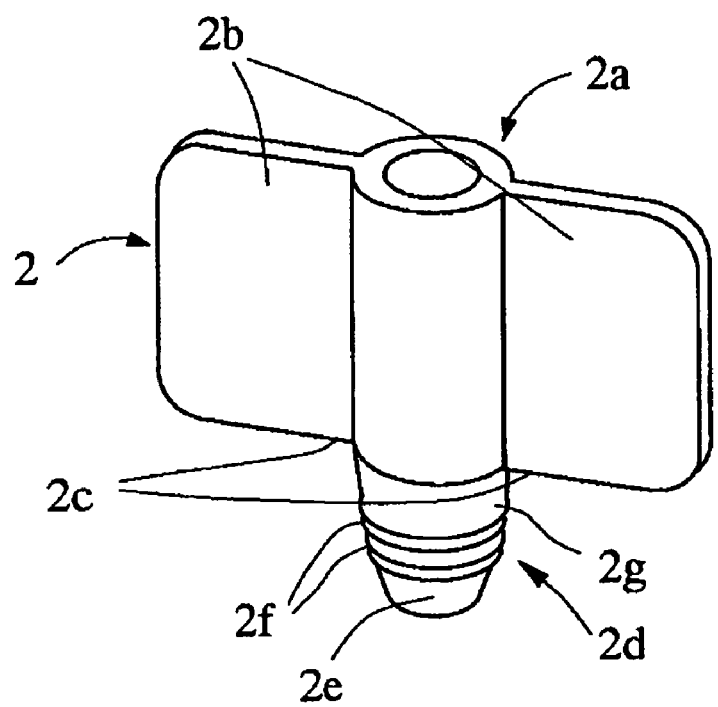
FIG. 3 is a perspective explanation view showing a state before plugging the plugging type dental liquid housing container of FIG. 1.
Figure 3:
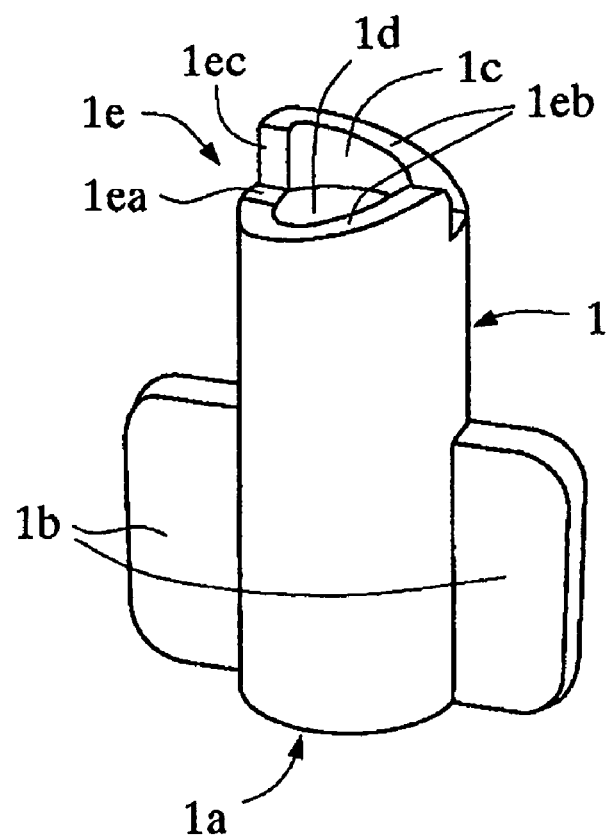
Figure 5:
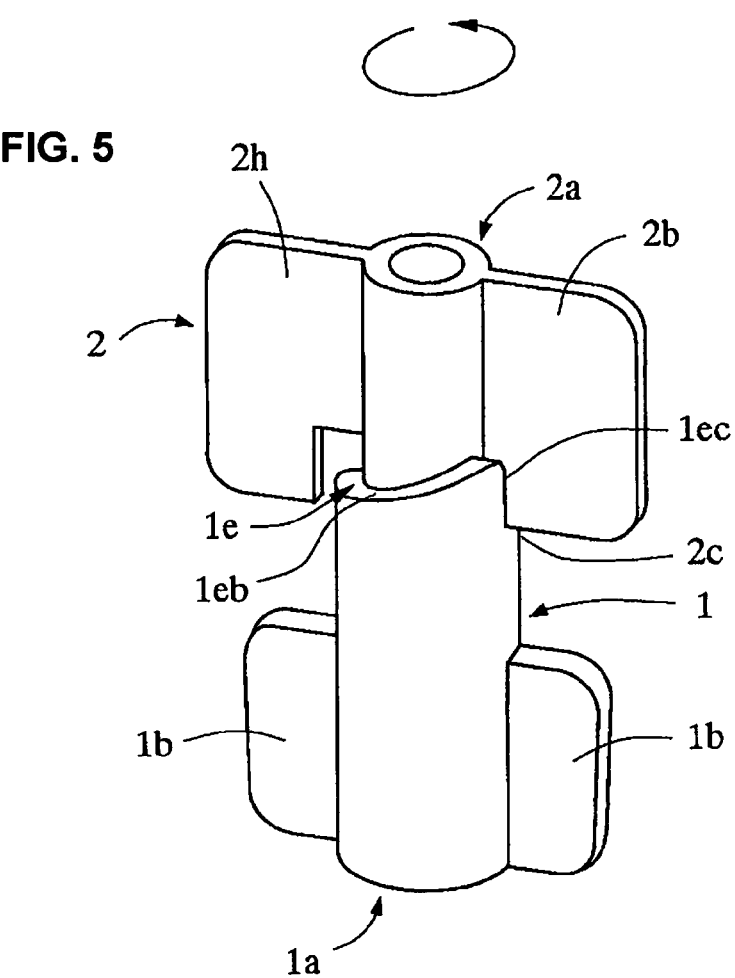
FIG. 5 is a perspective explanation view of another example of the plugging type dental liquid housing container according to the present invention.

Further, as illustrated in FIGS. 1 to 3, the contacting blade plates 2b may be respectively projected at one pair of positions facing each other on the plug part main body 2a, and the flat faces 1ea, the slope faces 1eb and the stepped faces 1ec may be respectively formed at one pair of positions facing each other on the end face 1e. In such a constitution, each of the end faces 2c of the contacting blade plates 2b, which are projected at one pair of positions facing each other, is moved along each slope face 1eb formed at the opening end of the liquid housing part 1a. Thus, since the plug main body 2a of the plug body 2 is pushed upwardly at one pair of positions facing each other, the plug body 2 is lifted uprightly without falling sideways. Thus, the container can be opened smoothly and easily only by half-rotating the plugged plug body 2, so that it is preferable. Further, when the plugging type dental liquid housing container is smaller one, one slope face 1eb may be formed in order to obtain the sufficiently long slope face 1eb, as illustrated in FIG. 5. Further, when the plugging type dental liquid housing container is large, three or more slope faces 1eb may be formed in order to open the container with a small rotation angle, although not illustrated in the drawings. At this time, it is preferable that the number of the contacting blade plate 2b of the plug body 2, which is contacted with the slope face 1eb or the like, is changed corresponding to the number of the slope face 1eb.

Further, it is preferable that the container main body 1 and the plug body 2 are made of the ethylene-tetracyclododesene copolymer, which has low temperature dependency and can keep the rigidity even at high temperature, in order to keep the high sealability. However there is the problem that the container main body 1 and the plug body 2, which are made of the material having the high ratio of the ethylene-tetracyclododesene copolymer, are easily self-fused. Therefore, in such a case, it is preferable that the container main body 1 is made of the mixture of the ethylene-tetracyclododesene copolymer of 90% or more by weight and polyethylene, the plug body 2 is made of the mixture of the ethylene-tetracyclododesene copolymer of 50% or more by weight and polyethylene, and at least one of ethylene-tetracyclododesene copolymer contained in the container main body 1 and the plug body 2 is less than 95% by weight. Then, the high rigidity can be kept, and the container main body 1 and the plug body 2 are not self-fused.

Figure 6:
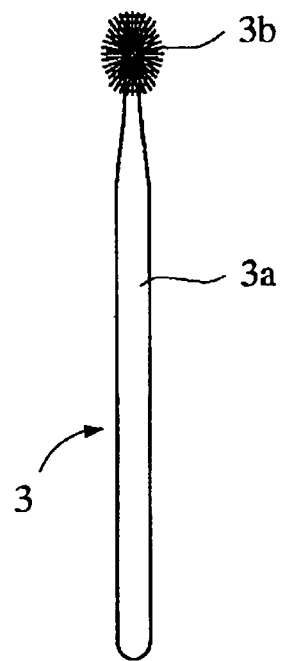
FIG. 6 is a front explanation view of one example of a liquid taking out tool.

3 is a liquid taking out tool, where a liquid adsorbent 3b is mounted on one end of a rod-shaped part 3a extending to the bottom part of the liquid housing part 1a when inserted into the liquid housing part 1a of the container main body 1. By using the liquid taking out tool 3, when only a few amount of the liquid housed in the liquid housing part 1a remains or the liquid has the high viscosity, the liquid can be taken out easily. Further, when the liquid adsorbed to the liquid adsorbent 3b is used as it is, the dental treatment can be carried out without soiling the hand, so that it is preferable. As the liquid adsorbent 3b of the liquid taking out tool 3, although a blush-shaped tool as illustrated in FIG. 6 can be preferably used, it is not necessarily limited to this, and a cotton ball-shaped tool or the like may be used.

Figure 4:
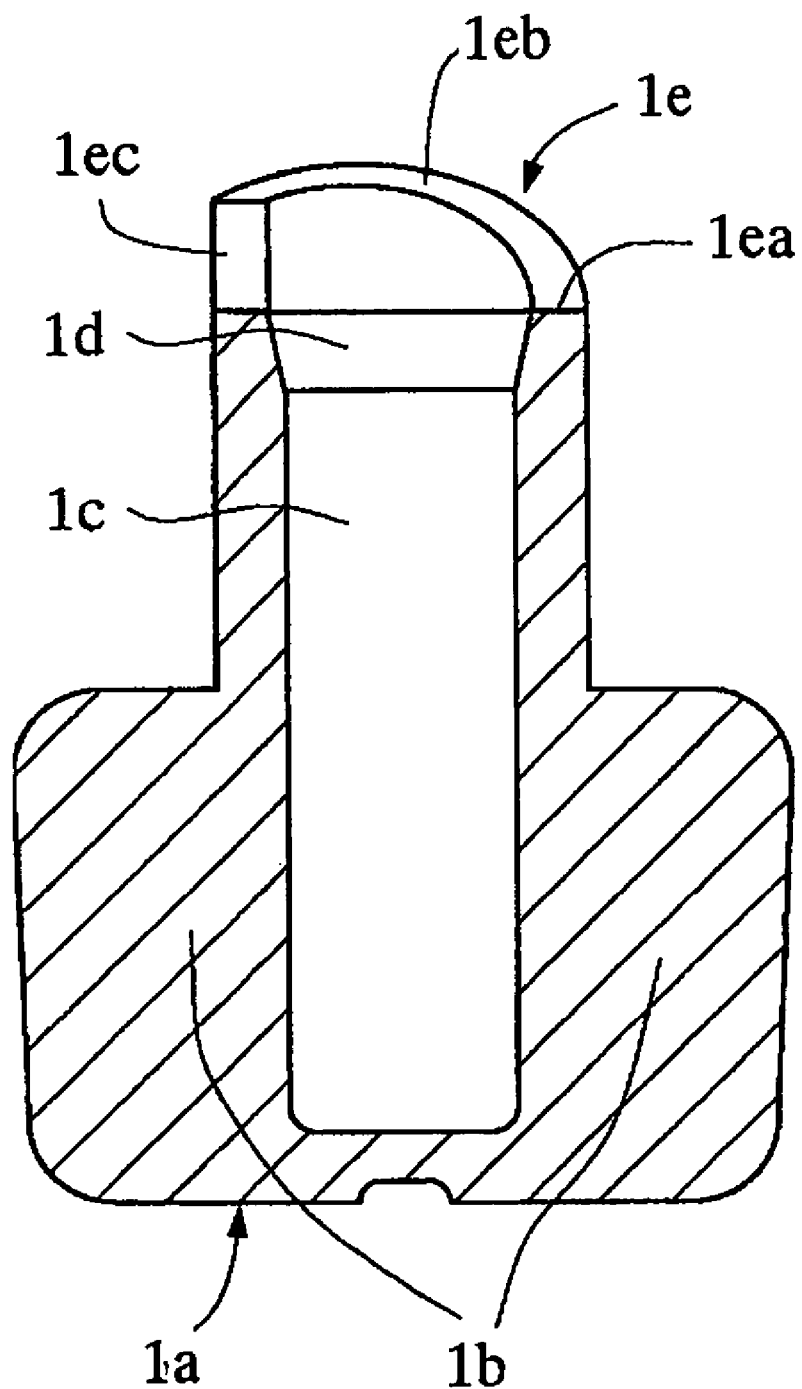
FIG. 4 is a front cross-sectional explanation view of a container main body of FIG. 3.

In order to actually seal the dental liquid in the plugging type dental liquid housing container according to the present invention having such the constitutions, it can be done only by pouring the dental liquid into the liquid housing part 1a of the container main body 1, inserting the plug main body 2a of the plug body 2 into the liquid housing part 1a of the container main body 1 from the sealing plug part 2d side, where the state before the insertion of the plug body 2 is illustrated in FIG. 3, and hitting the plug 2 to contact the end face 2c at the plug main body 2a side of the lower face of the contacting blade plate 2b with the flat face 1ea of the end face 1e of the container main body 1. Further, as illustrated in FIG. 4, the inner face taper part 1d, which has an inner diameter gradually decreasing toward the bottom part side from at least the flat face, is formed on the opening part side of the inner face 1c of the liquid housing part 1a, and the inner face 1c, which follows to the inner face taper part 1d, is formed to have the cylindrical shape having the small diameter. Thus, since the diameter of the opening part side of the liquid housing part 1a is large, the plug main body 2a of the plug body 2 can be easily inserted. Further, when the plug body taper part 2g, which is to be contacted with the inner face taper part 1d of the liquid housing part 1a, is formed on the upper side of the annular projection ridge parts 2f of the sealing plug part 2d, the plug body taper part 2g of the plug body 2 is contacted with the inner face taper part 1d of the liquid housing part 1a by plugging the plug body 2. Further, since the plural annular projection ridge parts 2f is contacted with the inner face 1c, which follows the inner taper part 1d, the container main body 1 is multiply sealed with the plug body 2. Further, since the plural annular projection ridge parts 2f contacted with the inner face 1c of the liquid housing part 1a is formed as illustrated in FIG. 3, each annular projection ridge part 2f is flexible and can be deformed according to the shape of the inner face 1c of the liquid housing part 1a, when plugging the plug body 2. Then, the plug 2 can be closely fitted easily, and the high sealability can be kept. Further, while the plugging type dental liquid housing container according to the present invention is transported and stored in this state, it can keep the high sealability by the annular projection ridge parts 2f even when the position of the plug body 2 is somewhat moved at this time. Since the container can be easily sealed only by plugging in this way, a dental liquid product can be easily produced using the plugging type dental liquid housing container according to the present invention.

Then, in order to open the plugging type dental liquid housing container, it can be done, in the case of the embodiment illustrated in FIGS. 1 to 4, by holding the holding blade plate 1b of the container main body 1 and the contacting blade plate 2b of the plug body 2, rotating the plug body 2 counterclockwise with respect to the container main body 1 from the state of FIG. 1, moving the end face 2c on the plug main body 2a side of the lower face the contacting blade plate 2b along the slope face 1eb from the flat face 1ea of the end face 1e, and gradually lifting the plug body 2. Then, the container can be easily opened in such the way without extracting the plug body 2 by force. Further, the rotating direction of the plug 2 may be a clockwise direction, although it is a counterclockwise in this embodiment. In anyway, even if the plug 2 or the container main body 1 is to be rotated in the mistaken direction, the contacting blade plate 2b of the plug body 2 cannot be rotated since it is contacted with the stepped face 1ec of the end face 1e of the container main body 1, as illustrated in FIG. 1. Thus, anyone can handle this container easily without hesitating the choice of the rotation direction of the plug body when using it. Further, the annular projection ridge parts 2f of the plug body 2 are not positioned at the inner taper part 1d of the liquid housing part 1a where the inner diameter becomes large, unless the plug 2 is rotated by a predetermined angle (half-rotated in the case of the embodiment illustrated in FIGS. 1 to 4) so that the end face 2c on the plug main body 2a side of the lower face of the contacting blade plate 2b is moved along the slope face 1eb of the end face 1e of the opening end of the liquid housing part 1a to reach to the top end thereof. Thus, since the plug body 2 cannot be opened by rotating it only somewhat, the sealability is high, and the handling is easy. Further, in the case of the embodiment illustrated in FIG. 5, the container can be easily opened by holding the contacting blade plate 2b and the holding blade plate 2h of the plug body 2, and rotating the plug body 2 one time in counterclockwise direction with respect to the container main body 1 from the state of FIG. 5.

Further, when the container main body 1 or the plug body 2 is deformed by temperature change at the time of the transportation or the storage, the high sealability cannot be kept. Thus, it is preferable that the container main body 1 and the plug body 2 are made of the material such as ethylene-tetracyclododesene copolymer, which has the low temperature dependency and can keep the high rigidity even at high temperature. However, when the dental liquid to be housed in the container is the liquid dissolved with the organic solvent having high volatility, such as the dental adhesives, primer or the like, using acetones or esters as a solvent, there is the problem that the container main body 1 and the plug body 2 formed by the material having a high ratio of the ethylene-tetracyclododesene copolymer are self-fused and the container, it cannot be opened thereby. Therefore, the container main body 1 is made of the mixture of the ethylene-tetracyclododesene copolymer of 90% or more by weight and polyethylene, the plug body 2 is made of the mixture of the ethylene-tetracyclododesene copolymer of 50% or more by weight and polyethylene, and at least one of ethylene-tetracyclododesene copolymer contained in the container main body 1 and the plug body 2 is less than 95% by weight. Since the container main body 1, which is generally susceptible to the temperature change when exposing in the external air, is formed with the material comprising the ethylene-tetracyclododesene copolymer of 90% or more by weight, it has the low temperature dependency and the high rigidity can be kept even at high temperature. The plug body 2 inserted into the container main body is not susceptible to the external temperature influence. Thus, even when the plug body 2 is formed with the material comprising the ethylene-tetracyclododesene copolymer of 50% or more by weight, the high rigidity can be sufficiently kept. Further, since at least one of ethylene-tetracyclododesene copolymer contents of the container main body 1 and the plug body 2 is less than 95% by weight, the container main body 1 and the plug body 2 are not self-fused, so that it is preferable. In addition, as a commercial material satisfying such the conditions, for example, Apel (commercial name) produced by Mitsui Chemical Corporation can be used.

Further, in order to actually use the dental liquid in the plugging type dental liquid housing container after opening this container, the method varies with a kind of the dental liquid and a dental treatment method. However, when the amount of the liquid housed in the liquid housing part 1a is a few or this liquid has the high viscosity, the liquid taking out tool 3, which has the liquid adsorbent 3b at one end of the rod-shaped part 3a as illustrated in FIG. 6, can be preferably used. In such a case, the dental liquid can be easily taken out, and the liquid absorbed to the liquid adsorbent 3b can be used as it is, so that the dental treatment can be carried out without soiling the hand.

What is claimed is:

1. The plugging type dental liquid housing container, comprising,
    a container main body having a holding blade plate projected on an outer circumference face of a cylindrical liquid housing part which has an opening upper end and a closing bottom part, and
    a plug body having a sealing plug part at a lower end thereof, and a contacting blade plate projected on an outer circumference face of a plug main body which is provided starting from an upper end of the sealing plug part,
    wherein the container main body comprises,
    a flat face, which is rectangular with a center axis of the liquid housing part and is contacted with an end face being at the plug main body side and on a lower face of the contacting blade plate, when the plug body is plugged,
    a slope face inclined to be raised in a predetermined direction from one end of the flat face,
    a stepped face fallen to another end of the flat face from a top point of the slope face, and
    an inner face taper part having an inner diameter gradually decreasing toward a bottom part side from at least the flat face, the slope face and the stepped face being formed at an end face of an opening end of the liquid housing part, the inner face taper part being formed on an opening part side of an inner face of the liquid housing part, and wherein
    the sealing plug part of the plug body comprises,
    a truncated conical shape part tapered toward the lower end, and
    plural annular projection ridge parts on an upper side of the truncated conical shape part, which are contacted with a portion on the bottom part side of the inner face taper part of the inner face of the liquid housing part of the container main body, and positioned at the inner face taper part of the liquid housing part when the plug body is rotated to move the end face of the contacting blade plate along the slope face of the end face of the opening end of the liquid housing part to the top point of the slope face.

2. The plugging type dental liquid housing container as claimed in claim 1,
    wherein a plug body taper part, which is contacted with the inner face taper part of the liquid housing part of the container main body, is formed on the upper side of the annular projection ridge parts of the sealing plug part of the plug body.

3. The plugging type dental liquid housing container as claimed in claim 2,
    wherein contacting blade plates are respectively projected at one pair of positions facing each other on the plug main body of the plug body, and flat faces, slope faces and stepped faces are respectively formed at one pair of positions facing each other on the end face of the opening end of the liquid housing part of the container main body.

4. The plugging type dental liquid housing container as claimed in claim 3,
    wherein a holding blade plate for holding the plug is further projected on the outer circumference face at the upper side from the sealing plug part of the plug main body of the plug body, so as not to contact with the container main body when plugging or removing the plug body.

5. The plugging type dental liquid housing container as claimed in claim 3,
    wherein the container further comprises a liquid taking out tool where a liquid adsorbent is mounted on one end of a rod-shaped part extending to the bottom part of the liquid housing part when inserting it into the liquid housing part of the container main body.

6. The plugging type dental liquid housing container as claimed in claim 2,
    wherein a holding blade plate for holding the plug is further projected on the outer circumference face at the upper side from the sealing plug part of the plug main body of the plug body, so as not to contact with the container main body when plugging or removing the plug body.

7. The plugging type dental liquid housing container as claimed in claim 2,
    wherein the container main body is made of a mixture of an ethylene-tetracyclododesene copolymer of 90% or more by weight and polyethylene, the plug body is made of a mixture of an ethylene-tetracyclododesene copolymer of 50% or more by weight and polyethylene, and at least one of ethylene-tetracyclododesene copolymer contained in the container main body and the plug body is less than 95% by weight, when the liquid to be housed in the liquid housing part of the container main body is a dental liquid dissolved with an organic solvent having high volatility.

8. The plugging type dental liquid housing container as claimed in claim 2,
    wherein the container further comprises a liquid taking out tool where a liquid adsorbent is mounted on one end of a rod-shaped part extending to the bottom part of the liquid housing part when inserting it into the liquid housing part of the container main body.

9. The plugging type dental liquid housing container as claimed in claim 1,
    wherein contacting blade plates are respectively projected at one pair of positions facing each other on the plug main body of the plug body, and flat faces, slope faces and stepped faces are respectively formed at one pair of positions facing each other on the end face of the opening end of the liquid housing part of the container main body.

10. The plugging type dental liquid housing container as claimed in claim 9,
    wherein a holding blade plate for holding the plug is further projected on the outer circumference face at the upper side from the sealing plug part of the plug main body of the plug body, so as not to contact with the container main body when plugging or removing the plug body.

11. The plugging type dental liquid housing container as claimed in claim 9,
    wherein the container further comprises a liquid taking out tool where a liquid adsorbent is mounted on one end of a rod-shaped part extending to the bottom part of the liquid housing part when inserting it into the liquid housing part of the container main body.

12. The plugging type dental liquid housing container as claimed in claim 1,
    wherein a holding blade plate for holding the plug is further projected on the outer circumference face at the upper side from the sealing plug part of the plug main body of the plug body, so as not to contact with the container main body when plugging or removing the plug body.

13. The plugging type dental liquid housing container as claimed in claim 1,
wherein the container main body is made of a mixture of an ethylene-tetracyclododesene copolymer of 90% or more by weight and polyethylene, the plug body is made of a mixture of an ethylene-tetracyclododesene copolymer of 50% or more by weight and polyethylene, and at least one of ethylene-tetracyclododesene copolymer contained in the container main body and the plug body is less than 95% by weight, when the liquid to be housed in the liquid housing part of the container main body is a dental liquid dissolved with an organic solvent having high volatility.

14. The plugging type dental liquid housing container as claimed in claim 1,
wherein the container further comprises a liquid taking out tool where a liquid adsorbent is mounted on one end of a rod-shaped part extending to the bottom part of the liquid housing part when inserting it into the liquid housing part of the container main body.

* * * * *